United States Patent
Park et al.

(10) Patent No.: US 7,857,141 B2
(45) Date of Patent: Dec. 28, 2010

(54) APPARATUS AND METHOD FOR SEPARATING COMPONENTS

(75) Inventors: Jong-myeon Park, Seoul (KR); Byung-chul Kim, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 623 days.

(21) Appl. No.: 11/850,258

(22) Filed: Sep. 5, 2007

(65) Prior Publication Data

US 2008/0135462 A1    Jun. 12, 2008

(30) Foreign Application Priority Data

Dec. 11, 2006  (KR) ...................... 10-2006-0125659
Apr. 11, 2007  (KR) ...................... 10-2007-0035730

(51) Int. Cl.
*B03B 5/60*   (2006.01)
*B03D 1/00*   (2006.01)

(52) U.S. Cl. ..................... 209/199; 209/192; 209/194; 422/72; 435/289.1

(58) Field of Classification Search ................ 209/192, 209/194, 199; 422/72; 435/289.1
See application file for complete search history.

(56) References Cited

U.S. PATENT DOCUMENTS

| | | | |
|---|---|---|---|
| 6,632,399 B1 * | 10/2003 | Kellogg et al. | 422/72 |
| 7,476,326 B2 * | 1/2009 | Ahn et al. | 210/767 |
| 2004/0191125 A1 * | 9/2004 | Kellogg et al. | 422/72 |
| 2005/0026301 A1 * | 2/2005 | Petithory | 436/180 |
| 2005/0109396 A1 | 5/2005 | Zucchelli et al. | |
| 2005/0126312 A1 | 6/2005 | Bedingham et al. | |
| 2007/0280859 A1 * | 12/2007 | Kido et al. | 422/100 |
| 2008/0262213 A1 * | 10/2008 | Wu et al. | 536/25.4 |

* cited by examiner

*Primary Examiner*—Stefanos Karmis
*Assistant Examiner*—Terrell H Matthews
(74) *Attorney, Agent, or Firm*—Sughrue Mion, PLLC

(57) ABSTRACT

An apparatus for separating components and a method of separating components using the apparatus are provided. The apparatus includes: a main chamber which contains a sample that is separated into a plurality of layers by a centrifugal force; a component separating chamber which is connected to the main chamber, and receives a specific layer including specific components among the plurality of layers; a first channel which connects the component separating chamber to the main chamber; and a first channel valve which is disposed in the first channel to control a liquid flowing through the first channel.

34 Claims, 14 Drawing Sheets

APPARATUS AND METHOD FOR SEPARATING COMPONENTS

CROSS-REFERENCE TO RELATED PATENT APPLICATIONS

This application claims priority from Korean Patent Application No. 10-2006-0125659, filed on Dec. 11, 2006, and Korean Patent Application No. 10-2007-0035730, filed on Apr. 11, 2007, in the Korean Intellectual Property Office, the disclosures of which are incorporated herein in their entirety by reference.

BACKGROUND OF THE INVENTION

1. Field of the Invention

Apparatuses and methods consistent with the present invention relate to separating specific components from a sample.

2. Description of the Related Art

Recently, separation of specific components, such as white blood cells (WBCs) from whole blood (WB), has been widely used as a method for diagnosing multiple diseases. Specific components, such as WBCs, can be extracted from a sample, such as blood, by sequentially extracting through chemical procedures components other than the specific components until only the specific components are left, or by separating the sample into a plurality of layers according to components and separating out a specific layer including a great number of the specific components through centrifugation.

FIGS. 1A and 1B are cross-sectional views sequentially illustrating a related art method of separating WBCs from WB through centrifugation.

Referring to FIG. 1A, to extract the WBCs from the WC, 100 μl of a density gradient medium (DGM) 20, which is a reagent, is injected into a tube 10, and a diluted blood solution 22 containing a mixture of 100 μl of WB, 100 μl of salt solution having a concentration of 0.9%, and a small amount of anticoagulant is injected into the tube 10 to be overlaid on the reagent 20. When the tube 10 is centrifuged so that a centrifugal force can be applied in a direction indicated by arrow F, a plurality of layers are formed in the tube 10 according to components due to density difference. A lowermost first layer 31 is a deep red liquid containing a great number of red blood cells (RBCs), a second layer 32 formed on the first layer 31 is a colorless liquid containing a great number of WBCs, and an uppermost third layer 33 is a pale red liquid hardly containing RBCs and WBCs. The second layer 32 containing the WBCs can be manually extracted from the plurality of layers using a pipette 15.

However, the related art method using centrifugation is performed by manually injecting the DGM 20 and the diluted blood solution 22 into the tube 10 and manually extracting the second layer 32 from the tube 10. Accordingly, a sufficient number of WBCs may not be obtained and the WBCs may be contaminated during these operations according to an operator's skill level.

SUMMARY OF THE INVENTION

The present invention provides an apparatus for separating components, which does not require a delicate manual operation and thus can lead to a constant yield regardless of an operator's skill level, and a method of separating components using the apparatus.

Exemplary embodiments of the present invention overcome the above disadvantages and other disadvantages not described above. Also, the present invention is not required to overcome the disadvantages described above, and an exemplary embodiment of the present invention may not overcome any of the problems described above.

According to an aspect of the present invention, there is provided an apparatus for separating components, the apparatus comprising: a main chamber containing a sample that is separated into a plurality of layers by a centrifugal force; a component separating chamber connected to the main chamber, and containing a specific layer including specific components among the plurality of layers; a first channel connecting the component separating chamber to the main chamber; and a first channel valve disposed in the first channel to control a liquid flowing through the first channel.

The main chamber and the component separating chamber may be formed on a single substrate.

The apparatus may further comprise a rotating unit rotating the substrate.

The main chamber may extend in a direction parallel to the direction of a centrifugal force produced by the rotation of the substrate.

The component separating chamber may be disposed to pump the specific layer from the main chamber into the component separating chamber due to the centrifugal force produced by the rotation of the substrate.

The apparatus may further comprise: a waste chamber connected to a portion of the main chamber to which the component separating chamber is not connected, and receiving a layer not including the specific components among the plurality of layers formed in the main chamber; a second channel connecting the waste chamber to the main chamber; and a second channel valve disposed on the second channel to control a liquid flowing through the second channel.

The main chamber, the component separating chamber, and the waste chamber may be formed on a single substrate. The apparatus may further comprise a rotating unit rotating the substrate, wherein the waste chamber is disposed to pump the layer not including the specific components from the main chamber into the waste chamber due to a centrifugal force produced by the rotation of the substrate.

A plurality of component separating chambers may be used to extract and receive a plurality of specific layers among the plurality of layers formed in the main chamber, and first channels and first channel valves respectively correspond in number to the component separating chambers.

The plurality of component separating chambers may be connected to different portions of the main chamber.

The main chamber may comprise at least one pair of liquid containing parts, and at least one capillary tube connecting adjacent liquid containing parts.

Some of the liquid containing parts may contain the sample, the remaining ones of the liquid containing parts may contain a reagent that reacts with the sample and helps the sample to be separated into the plurality of layers, and the capillary tube may isolate the sample from the reagent before the sample is separated into the plurality of layers.

The valve in the apparatus may include a phase change material that closes its corresponding channel and is in a solid state at room temperature and is in a liquid state when supplied with energy. The apparatus may further comprise an energy source supplying energy to the valve and opening the corresponding channel.

The valve may further comprise a plurality of micro heating particles dispersed in the phase change material and producing heat when supplied with energy.

The energy source may emit an electromagnetic wave to the valve.

The energy source may include a laser source emitting a laser beam.

According to another aspect of the present invention, there is provided a method of separating specific components from a sample using an apparatus for separating components, the apparatus comprising a main chamber, a component separating chamber connected to the main chamber, a first channel connecting the component separating chamber to the main chamber, and a first channel valve disposed in the first channel, the method comprising: injecting the sample into the main chamber; separating the sample into a plurality of layers according to components; and opening the first channel valve and extracting and discharging a specific layer including the specific components among the plurality of layers to the component separating chamber.

The sample may be one selected from the group consisting of whole blood (WB), sputum, urine, and saliva.

The sample may be WB, and the extracting and discharging of the specific layer including the specific components may comprise extracting and discharging a specific layer including more specific components than any other layers to the component separating chamber.

The specific components discharged to the component separating chamber may be cells or viruses.

The cells may be white blood cells (WBC).

The sample may be WB, and the extracting and discharging of the specific layer including the specific components may comprise extracting and discharging a specific layer including a great number of specific components to the component separating chamber.

The method may further comprise injecting a reagent, which reacts with the sample and helps the sample into the plurality of layers, into the main chamber.

The reagent may be a density gradient medium (DGM).

The injecting of the reagent into the main chamber may precede the injecting of the sample into the main chamber.

The main chamber of the apparatus may comprise at least one pair of liquid receiving parts and at least one capillary tube connecting adjacent liquid receiving parts. Before the separating of the sample into the plurality of layers, the sample and the reagent may be injected into different liquid receiving parts of the main chamber such that the sample and the reagent are isolated from each other with the capillary tube therebetween.

The separating of the sample into the plurality of layers may comprise applying a centrifugal force to the sample contained in the main chamber and accelerating the separation of the sample into the plurality of layers.

The extracting and discharging of the specific layer including the specific components may comprise applying a centrifugal force to the plurality of layers and pumping the specific layer from the main chamber into the component separating chamber.

The apparatus may further comprise a waste chamber connected to a portion of the main chamber to which the component separating chamber is not connected, a second channel connecting the waste chamber to the main chamber, and a second channel valve disposed on the second channel. After the separating of the sample into the plurality of layers, the method may further comprise opening the second channel closed by the second channel valve and discharging a layer not including the specific components among the plurality of layers to the waste chamber.

The discharging of the layer not containing the specific components to the waste chamber may comprise applying a centrifugal force to the plurality of layers and pumping the layer not containing the specific components from the main chamber into the waste chamber.

The discharging of the layer not containing the specific components to the waste chamber may precede the extracting and discharging of the specific layer including the specific components.

The apparatus may comprises a plurality of component separating chambers, and first channels and first channel valves may respectively correspond in number to the component separating chambers, wherein the extracting and discharging of the specific layer including the specific components comprises respectively extracting and discharging the specific layers to the component separating chambers.

The valve in the apparatus may include a phase change material that closes its corresponding channel and is in a solid state at room temperature and in a liquid state when supplied with energy, wherein energy is supplied to the valve to open the corresponding channel.

The valve may further comprise a plurality of micro heating particles dispersed in the phase change material and producing heat when supplied with energy.

The energy supplied to the valve may be an electromagnetic wave.

The electromagnetic waves may be a laser beam.

BRIEF DESCRIPTION OF THE DRAWINGS

The above and other features and aspects of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

Figure 2:
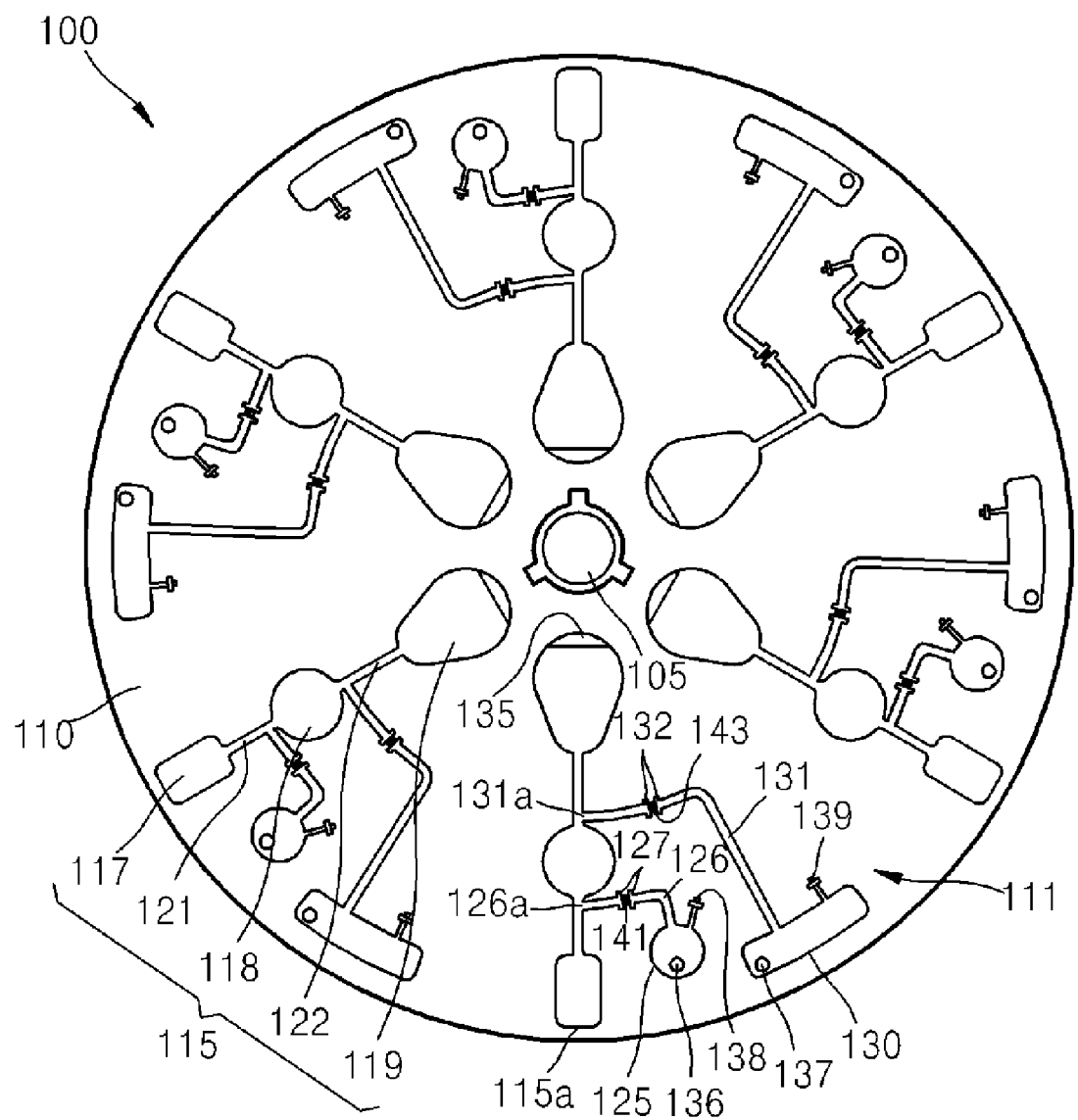
FIG. 2 is a plan view of an apparatus for separating components according to an exemplary embodiment of the present invention.

FIG. 2 is a plan view of an apparatus 100 for separating components according to an exemplary embodiment of the present invention.

Referring to FIG. 2, the apparatus 100 includes a disk-shaped substrate 110 with a radius of approximately 6 cm, and a spindle motor 105 rotating the substrate 110. The substrate 110 includes a plurality of component separating units 111 arranged at same angular intervals about the axis of the substrate 110. Each of the component separating units 111 includes a main chamber 115 radially extending from the axis of the substrate 110 in a direction parallel to a centrifugal force F (see FIG. 3B) produced by the rotation of the substrate 110, a component separating chamber 125, and a waste chamber 130. The component separating unit 111 further includes a first channel 126 connecting the component separating chamber 125 to the main chamber 115, and a second channel 131 connecting the waste chamber 130 to the main chamber 115. The first channel 126 and the second channel 131 are openably closed by a first channel valve 141 and a second channel valve 143, respectively.

The main chamber 115 contains a sample from which specific components are to be extracted, and may also contain a reagent that reacts with the sample and helps the sample to be separated into a plurality of layers according to components. The main chamber 115 includes first through third liquid receiving parts 117, 118, and 119, a first capillary tube 121 connecting the first liquid receiving part 117 to the second liquid receiving part 118, and a second capillary tube 122 connecting the second liquid receiving part 118 to the third liquid receiving part 119. An inlet hole 135 is formed in a top surface of the substrate 110 and allows a liquid to be injected into the main chamber 115 therethrough.

The component separating chamber 125 receives a specific layer including specific components desired to be extracted among the plurality of layers formed in the main chamber 115 (see FIG. 3C), and the waste chamber 130 contains layers not including the specific components. The component separating chamber 125 and the waste chamber 130 are disposed to pump the liquids contained in the main chamber 115 due to a centrifugal force produced by the rotation of the substrate 110. In detail, the component separating chamber 125 is closer to an outer circumference of the substrate 110 than a first channel connecting part 126a where the first channel 126 is connected to the main chamber 115, and the waste chamber 130 is farther away from the axis of the substrate 110 than a second channel connecting part 131a where the second channel 131 is connected to the main chamber 115.

The first channel connecting part 126a is farther away from the axis of the substrate 110 than the second channel connecting part 131a. In detail, the first channel connecting part 126a is located at a position where the second liquid receiving part 118 is connected to the first capillary tube 121, and the second channel connecting part 131a is located at a position where the second liquid receiving part 118 is connected to the second capillary tube 122.

A first outlet hole 136 is formed in the top surface of the substrate 110 and allows the liquid decanted into the component separating chamber 125 to be discharged to the outside of the substrate 110 therethrough. A second outlet hole 137 is formed in the top surface of the substrate 110 and allows the liquid decanted into the waste chamber 130 to be discharged to the outside of the substrate 110 therethrough. First and second vent holes 138 and 139 are formed in the top surface of the substrate 110 and allow air to enter and exit therethrough.

Each of the first channel valve 141 closing the first channel 126 and the second channel valve 143 closing the second channel 131 includes a phase change material, which is in a solid state at room temperature and in a liquid state when supplied with energy, and a plurality of micro heating particles uniformly dispersed in the phase change material and producing heat when supplied with energy. The phase change material may be wax. When heated, the wax is melted into a liquid and expanded. The wax may be selected from the group consisting of paraffin wax, microcrystalline wax, synthetic wax, and natural wax.

The phase change material may be a gel or a thermoplastic resin. The gel may be selected from the group consisting of polyacrylamide, polyacrylates, polymethacrylates, and polyvinylamides. Thermoplastic resin may be selected from the group consisting of cyclo olefin copolymer (COC), polymethylmethacrylate (PMMA), polycarbonate (PC), polystyrene (PS), polyoxymethylene (POM), perfluoroalkoxy (PFA), polyvinyl chloride (PVC), polypropylene (PP), polyethylene terephthalate (PET), polyetheretherketone (PEEK), polyamide (PA), polysulfone (PSU), and polyvinylidene fluoride (PVDF).

When laser beams or the like are applied to the micro heating particles, the temperature of the micro heating particles sharply increases such that the micro heating particles produce heat and are uniformly dispersed in the wax. To exhibit the properties, the micro heating particles may include a core including metallic components and a hydrophobic surface structure. For example, the micro heating particles may have a molecular structure consisting of a core formed of Fe and a plurality of surfactants combined with and surrounding the core.

In general, the micro heating particles are kept dispersed in a carrier oil. In order for the micro heating particles having the hydrophobic surface structure to be uniformly dispersed in the carrier oil, the carrier oil may be hydrophobic. A valve material may be prepared by mixing the carrier oil including the dispersed micro heating particles with the wax. The micro heating particles are not limited to the polymer particles, and may be quantum dots or magnetic beads.

Figure 4:
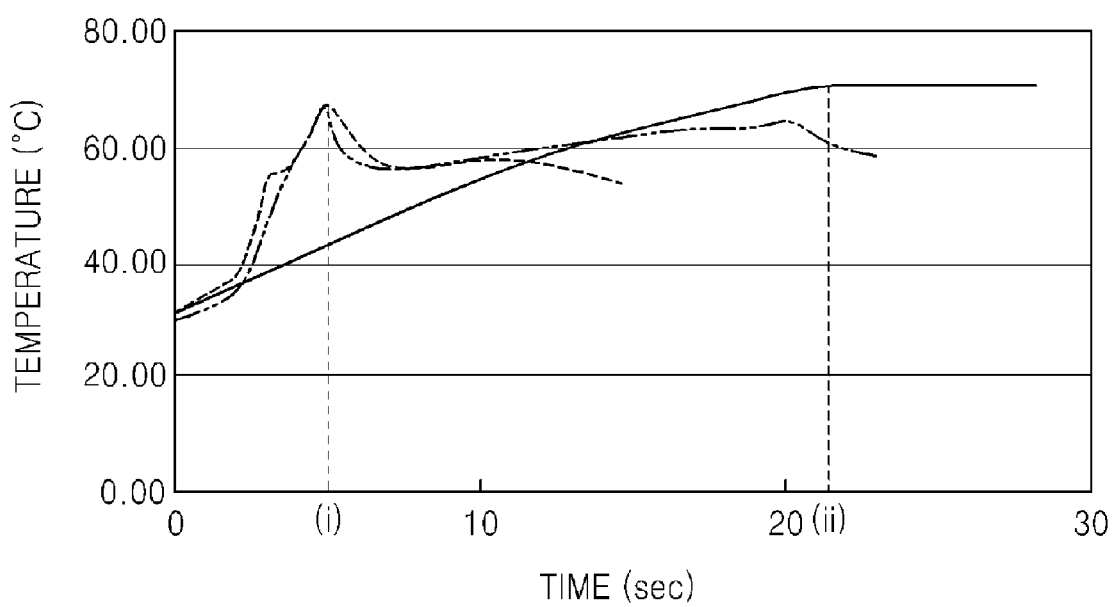
FIG. 4 is a graph illustrating time taken to reach a melting point when laser light is irradiated onto pure paraffin wax and paraffin wax including micro heating particles that are heated by laser irradiation.

FIG. 4 is a graph illustrating the time taken to reach a melting point when laser light is irradiated onto pure paraffin wax and paraffin wax containing micro heating particles that are heated by laser irradiation.

Referring to FIG. 4, a solid line represents the temperature of pure (100%) paraffin wax, a dotted line represents the temperature of paraffin wax containing 50% impurities (micro heating particles) in which a carrier oil including dispersed micro heating particles with an average diameter of 10 nm and paraffin wax are mixed in a ratio of 1:1, and a dot-dot-dashed line represents the temperature of paraffin wax containing 20% impurities (micro heating particles) in which a carrier oil including dispersed micro heating particles with an average diameter of 10 nm and paraffin wax are mixed in a ratio of 1:4. Laser beams having a wavelength of 808 nm were used in the experiment. The melting point of the paraffin wax is approximately 68 to 74° C. Referring to FIG. 4, the pure paraffin wax reaches the melting point 20 seconds or more after laser beams are irradiated (see ii). On the other hand, the paraffin wax containing the 50% impurities (micro heating particles) and the paraffin wax containing the 20% impurities (micro heating particles) are rapidly heated and reach the melting point approximately 5 seconds after laser irradiation (see i).

The micro heating particles may be made of a ferroelectric material such as Fe, Ni, Co, or an oxide thereof Alternatively, the micro heating particles may be made of a metal oxide such as $Al_2O_3$, $TiO_2$, $Ta_2O_3$, $Fe_2O_3$, $Fe_3O_4$, or $HfO_2$.

The apparatus 100 may include a laser source (not shown) as an energy source for supplying energy to the first and second channel valves 141 and 143 and opening the first channel 126 and the second channel 131. The laser source includes a laser diode that emits a laser beam that is a kind of electromagnetic wave. First drain groove 127 and second drain groove 132 are formed in the first channel 126 and the second channel 131, respectively.

The valve material including the phase change material and the micro heating particles is hardened on the first channel 126 to form the first channel valve 141, and the valve material is hardened on the second channel 131 to form the second channel valve 143. When the laser source emits laser beams to the first channel valve 141 for a while, the hardened valve material is melted and expanded explosively, and is received in the first drain groove 127 to open the closed first channel 126. Similarly, when the laser source emits laser beams to the second channel valve 143 for a while, the hardened valve material is melted and expanded explosively, and then is received in the second drain groove 132 to open the closed second channel 131. The energy source employed by the apparatus 100 is not limited to the laser source, and may be a source for emitting infrared rays (IRs) or high temperature gases to melt the first and second channel valves 141 and 143.

FIGS. 3A through 3E are plan views illustrating a method of separating components using the apparatus 100 of FIG. 2 according to an exemplary embodiment of the present invention. The method of separating the components will now be explained with reference to FIGS. 3A through 3E.

Figure 3A:
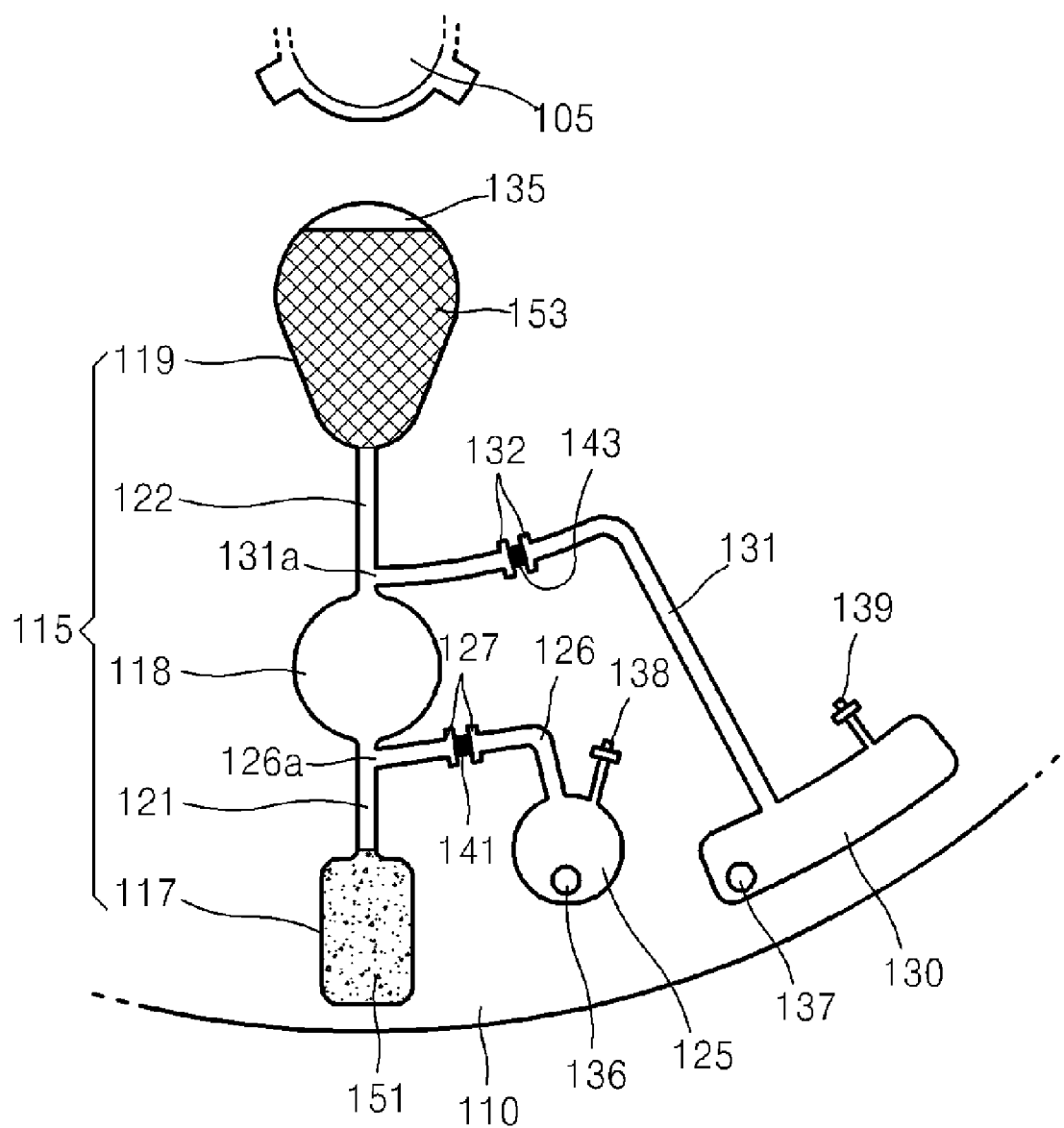
FIGS. 3A through 3E are partial cross-sectional views sequentially illustrating a method of separating components using the apparatus of FIG. 2 according to an exemplary embodiment of the present invention.

Referring to FIG. 3A, in order to separate white blood cells (WBC) from whole blood (WB), a reagent and a sample are injected into the main chamber 115. The reagent is a density grade medium (DGM) 151 and helps components of the WB to be separated into a plurality of layers according to density. The DGM 151 includes salts of alkali metals such as cesium chlorides, neutral, water-soluble molecules such as sucrose, hydrophilic macromolecules such as dextran gradients, and synthetic molecules. For example, the DGM 151 may be Lymphoprep™.

A manufacturer of the DGM 151, such as the Lymphoprep™, provides a set of conditions, that is, a protocol, for performing an experiment to separate specific components from a sample using the DGM supplied by the manufacturer. According to the protocol, the sample, that is, the WB, is diluted in salt solution and is injected into the main chamber 115. In detail, 100 µl of a DGM 151 is injected through the inlet hole 135 into the main chamber 115, and the spindle motor 105 is driven to pump the injected DGM 151 so that the DGM 151 is filled in the first liquid receiving part 117. A diluted blood solution 153 prepared by mixing 100 µl of WB, 100 µl of salt solution having a concentration of 0.9%, and a small amount of anticoagulant is injected through the inlet hole 135 into the main chamber 115. The diluted blood solution 153 is filled in the third liquid receiving part 119. The second liquid receiving part 118 and the first and second capillary tubes 121 and 122 are filled with air that is yet to be discharged. Accordingly, the DGM 151 in the first liquid receiving part 117 and the diluted blood solution 153 in the third liquid receiving part 119 are isolated from each other.

Figure 3B:
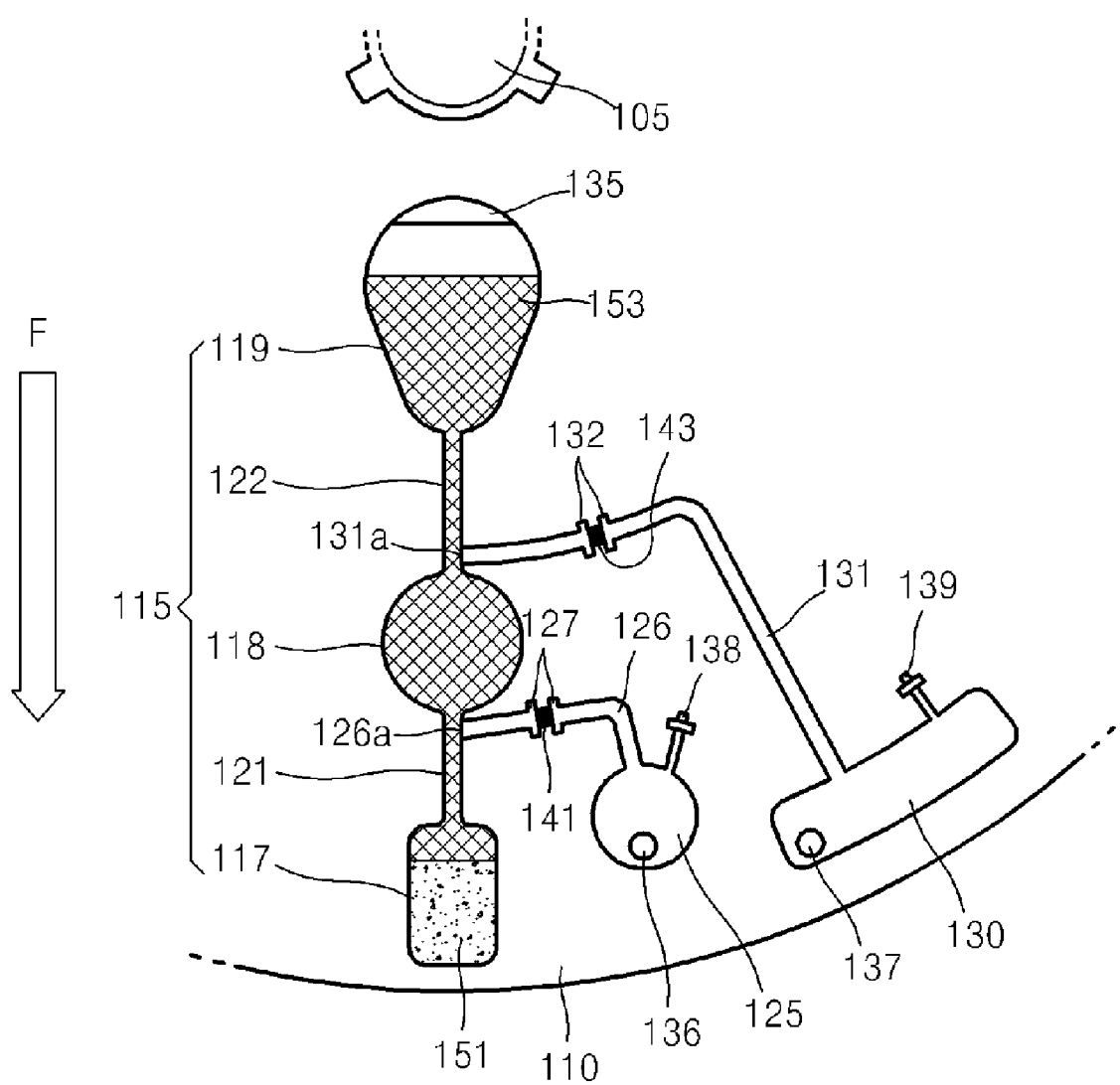

Referring to FIG. 3B, when the spindle motor 105 is driven again to rotate the substrate 110, the diluted blood solution 153 sequentially passes through the second capillary tube 122, the second liquid receiving part 118, and the first capillary tube 121, and gradually penetrates into the DGM 151. According to the protocol for the experiment, a centrifugal force of 700 to 800 G should be applied to centrifuge and separate the WBCs from the WB. Here, G denotes the gravitational acceleration. To apply a centrifugal force F of 700 to 800 G to the substrate 110 with the radius of approximately 6 cm, the substrate 110 should be rotated at 3000 to 3500 revolutions per minute (rpm).

Figure 3C:
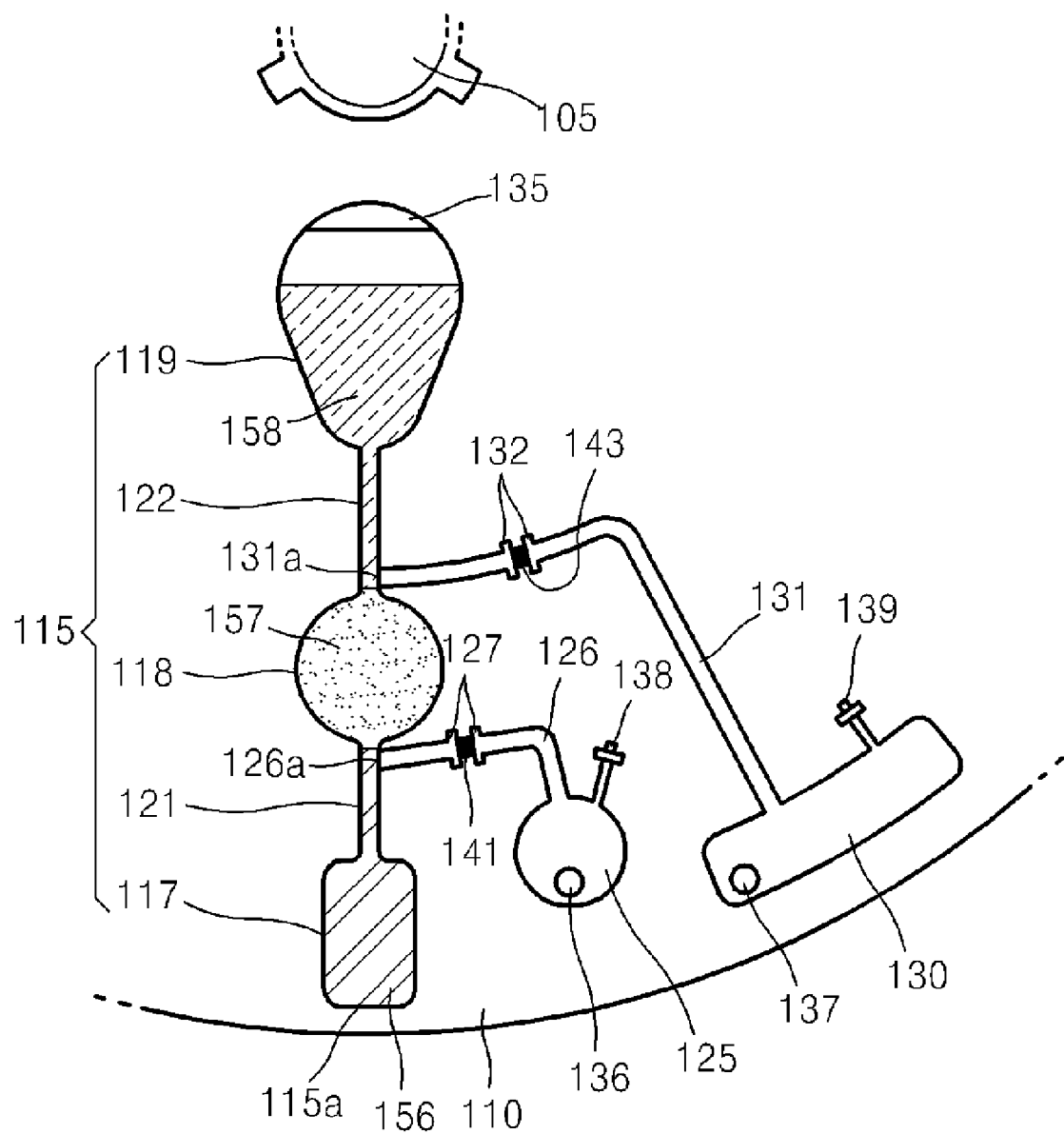

Referring to FIG. 3C, when the substrates 110 is rotated for 5 minutes or more at 3000 to 3500 rpm, the liquid in the main chamber 115 is separated into first through third layers 156, 157, and 158 according to density. The first through third layers 156, 157, and 158 are sequentially formed from an end 115a of the main chamber 115 adjacent to an outer circumference of the substrate 110. The first layer 156 is a deep red liquid containing a great number of RBCs, and has a highest density. The second layer 157 is a colorless liquid containing a great number of WBCs which are specific components desired to be extracted, and has a density less than that of the first layer 156. The third layer 158 is a pale red liquid hardly containing RBCs and WBCs, and has a lowest density.

Figure 1A:
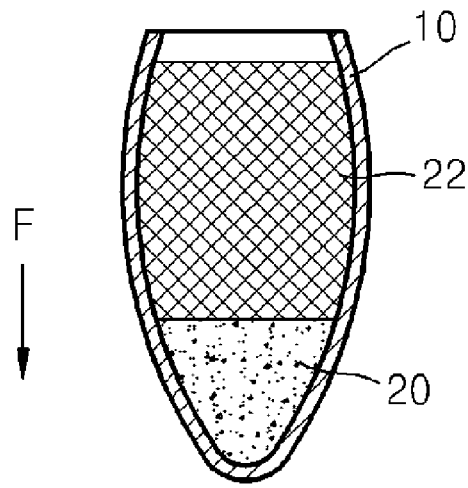
FIGS. 1A and 1B are cross-sectional views sequentially illustrating a related art method of separating white blood cells (WBC) from whole blood (WB)
Figure 1B:
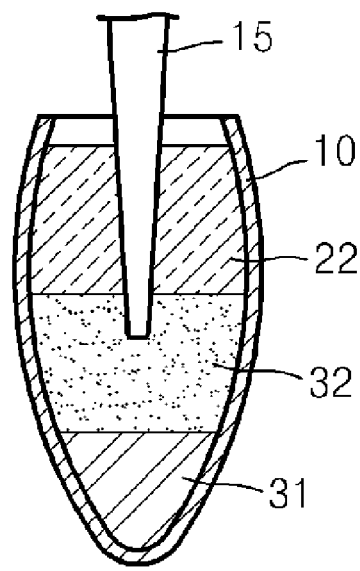

The interface between the first layer 156 and the second layer 157 is almost at the same level with the first channel connecting part 126a, and the interface between the second layer 157 and the third layer 158 is almost at the same level with the second channel connecting part 131a, because a related art method of separating components through centrifugation described with reference to FIGS. 1A and 1B is performed several times to obtain data and the positions of the first channel connecting parts 126a and the second channel connecting part 131a are determined based on the data.

Figure 3D:
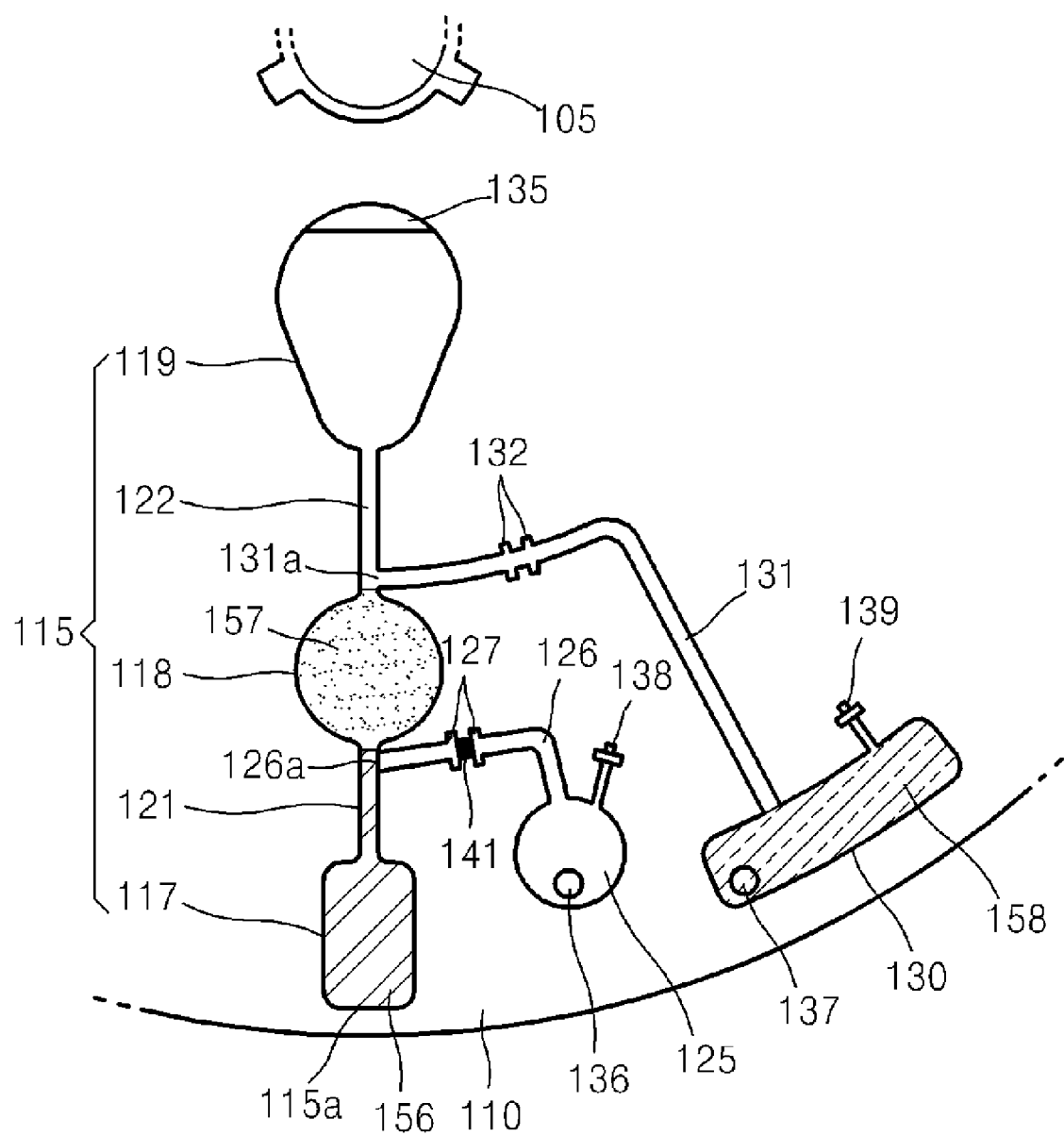

Referring to FIG. 3D, when the second channel valve 143 closing the second channel 131 is removed to open the second channel 131 and the spindle motor 105 is driven again to rotate the substrate 110, the third layer 158 is pumped and discharged from the main chamber 115 to the waste chamber 130. When the laser source emits a laser beam to the second channel valve 143, the valve material is melted and received in the second drain groove 132 to open the second channel 131. Since the third layer 158 contained in the waste chamber 130 is unnecessary for an operator, the third layer 158 is discarded.

Figure 3E:
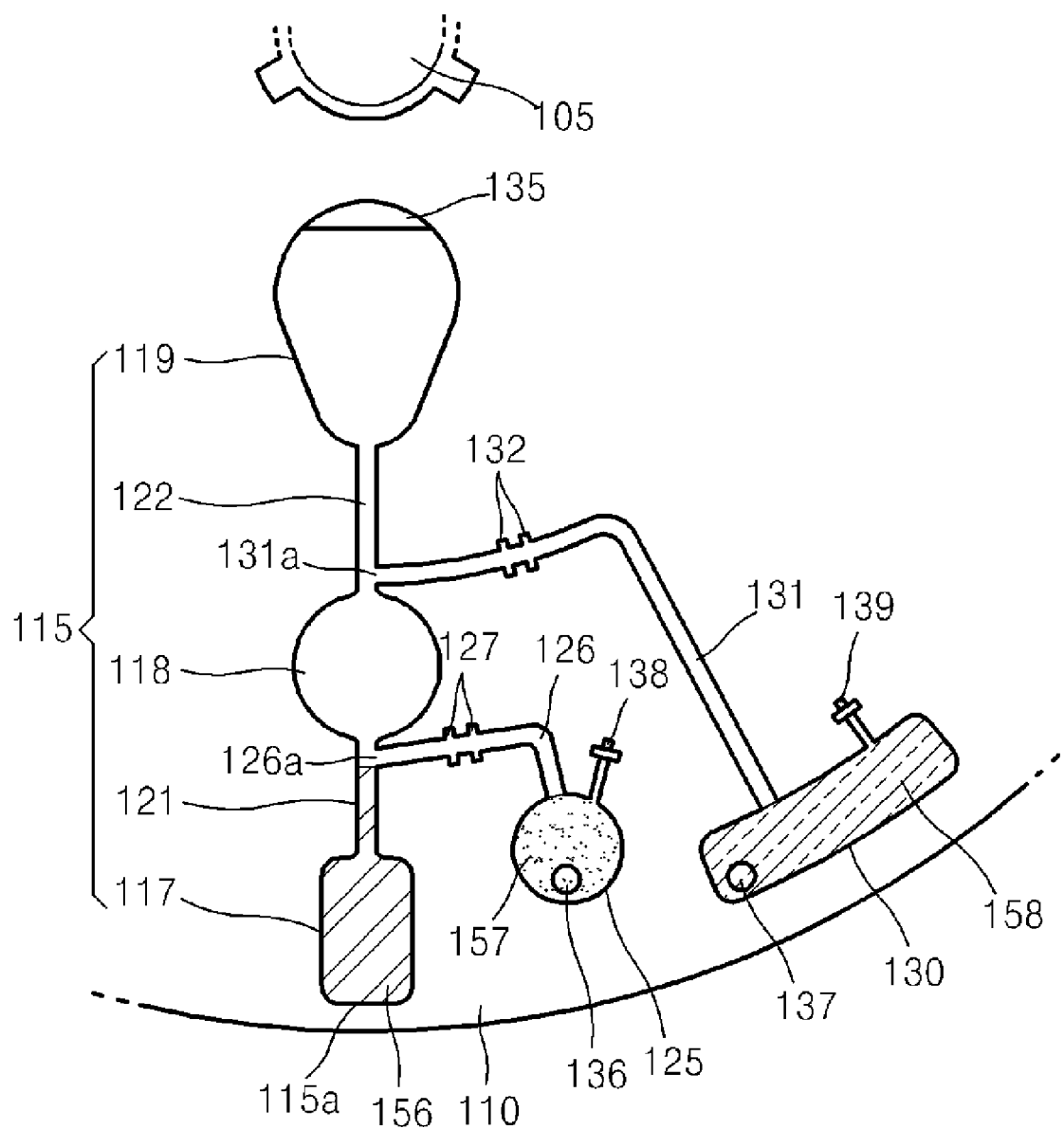

Referring to FIG. 3E, when the first channel valve 141 closing the first channel 126 is removed to open the first channel 126 and the spindle motor 105 is driven again to rotate the substrate 110, the second layer 157 is pumped and discharged from the main chamber 115 to the component separating chamber 125. When the laser source emits a laser beam to the first channel valve 141, the valve material is melted and received in the first drain groove 127 to open the first channel 126. Since the second layer 157 received in the component separating chamber 125 contains the specific components necessary for the operator, the second layer 157 is extracted through the first outlet hole 136.

A method of manufacturing the apparatus 100 will now be explained in detail with reference to FIGS. 1 and 2.

The substrate 110 of the apparatus 100 is made of silicon (Si), glass, or polymer. The substrate 110 is patterned by photolithography, and micromachined by etching or sandblasting to form the chambers 115, 125, and 130, the channels 126 and 131, and the holes 135, 136, 137, 138, and 139.

To determine the positions of the first channel connecting part 126a where the component separating chamber 125 is connected to the main chamber 115 and the second channel connecting part 131a where the waste chamber 130 is connected to the main chamber 115, the related art method of separating components through centrifugation described with reference to FIGS. 1A and 1B is performed several times and data are accumulated. The data include the volumes of first through third layers 31, 32, and 33 (see FIG. 1B), which are formed after a centrifugal force F is applied to a tube 10 (see FIG. 1A). Table 1 shows the volumes and averages of the first through third layers 31 through 33 obtained after the related art method for separating components through centrifugation was performed four times.

TABLE 1

|  | First experiment (μl) | Second experiment (μl) | Third experiment (μl) | Fourth experiment (μl) | Average (μl) |
|---|---|---|---|---|---|
| First layer | 71 | 56 | 73 | 67 | 67 |
| Second layer | 117 | 114 | 94 | 105 | 108 |
| Third layer | 112 | 130 | 133 | 127 | 126 |

It can be seen from Table 1 that the average volume of the specific layer, that is, the second layer 32, containing WBCs is 108 μl, and the average volume of the first layer 31 preceding the second layer is 67 μl. The first channel connecting part 126a is formed at a position spaced by a distance of 67 μl, corresponding to the average volume of the first layer 31, from the end 115a of the main chamber 115, when the first channel 126 is formed on the substrate 110. The second channel connecting part 131a is formed at a position spaced by a distance of 175 μl, corresponding to the sum of the average volume of the first layer 31 and the average volume of the second layer 32, from the end 115a of the main chamber 115, when the second channel 131 is formed on the substrate 110. As a result, the first channel connecting part 126a is located at the position where the second liquid receiving part 118 is connected to the first capillary tube 121, and the second channel connecting part 131a is located at the position where the second liquid receiving part 118 is connected to the second capillary tube 122 as described above.

Hence, the liquid discharged to the waste chamber 130 after the plurality of layers (see FIG. 3C) are formed includes most of the third layer 158 (see FIG. 3D), and includes no or a small amount of the second layer 157. The liquid discharged to the component separating chamber 125 includes most of the second layer 157 (see FIG. 3E) and includes no or a small amount of the first layer 156 or the third layer 158.

Figure 5:
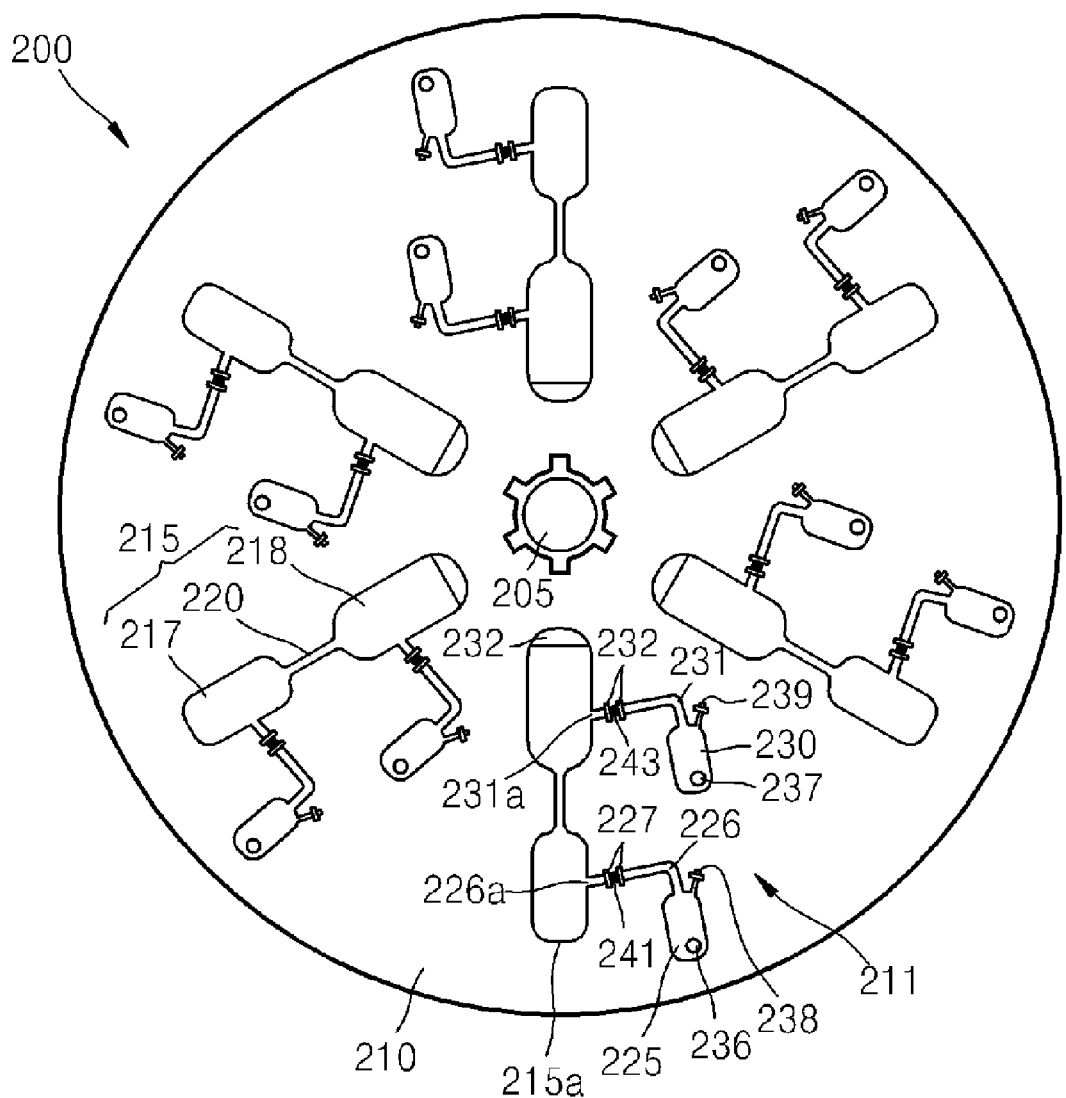
FIG. 5 is a plan view of an apparatus for separating components according to another exemplary embodiment of the present invention.

FIG. 5 is a plan view of an apparatus 200 for separating components according to another exemplary embodiment of the present invention. Since the apparatus 200 of FIG. 5 is similar to the apparatus 100 of FIG. 2, the description thereof will be made focusing on the difference therebetween.

Referring to FIG. 5, the apparatus 200 includes a substrate 210 including a plurality of component separating units 211 arranged at same angular intervals about the axis of the substrate 210, and a spindle motor 205 rotating the substrate 210. Each of the component separating units 211 includes a main chamber 215, a component separating chamber 225, a waste chamber 230, a first channel 226 connecting the component separating chamber 225 to the main chamber 215, and a second channel 231 connecting the waste chamber 230 to the main chamber 215. The first channel 226 and the second channel 231 are openably closed by a first channel valve 241 and a second channel valve 243, respectively.

The main chamber 215 includes first and second liquid receiving parts 217 and 218, and a capillary tube 220 connecting the first liquid receiving part 217 to the second liquid receiving part 218. A first channel connecting part 226a where the first channel 226 is connected to the main chamber 215 is located approximately in the middle of the first liquid receiving part 217, and a second channel connecting part 231a where the second channel 231 is connected to the main chamber 215 is located approximately in the middle of the second liquid receiving part 218.

In a top surface of the substrate 210, an inlet hole 235 is formed to allow a liquid to be injected into the main chamber 215 therethrough, a first outlet hole 236 is formed to allow a liquid decanted into the component separating chamber 225 to be discharged to the outside of the substrate 210 therethrough, a second outlet hole 237 is formed to allow a liquid decanted into the waste chamber 230 to be discharged to the outside of the substrate 210 therethrough, and first and second vent holes 238 and 239 are formed to allow air to enter and exit therethrough.

Each of the first channel valve 241 and the second channel valve 243 includes a phase change material that is in a solid state at room temperature and is in a liquid state when supplied with energy, and a plurality of micro heating particles uniformly dispersed in the phase change material and producing heat when supplied with energy. The apparatus 200 includes a laser source (not shown) as an energy source for supplying energy to the first and second channel valves 241 and 243 and opening the first channel 226 and the second channel 231. Since the first and second channel valves 241 and 243 have already been described with reference to the apparatus 100 of FIG. 2, a detailed explanation thereof will not be given. First drain grooves 227 and second drain grooves 232 are respectively formed in the first channel 226 and the second channel 231 and receive a valve material melted by laser irradiation.

FIGS. 6A through 6H are photographs sequentially illustrating experimental results obtained using a method of separating components using the apparatus 200 of FIG. 5 according to another exemplary embodiment of the present invention. Since the method of FIGS. 6A through 6H is similar to the method of FIGS. 3A through 3E, the following explanation will be made focusing on the difference therebetween.

Figure 6A:
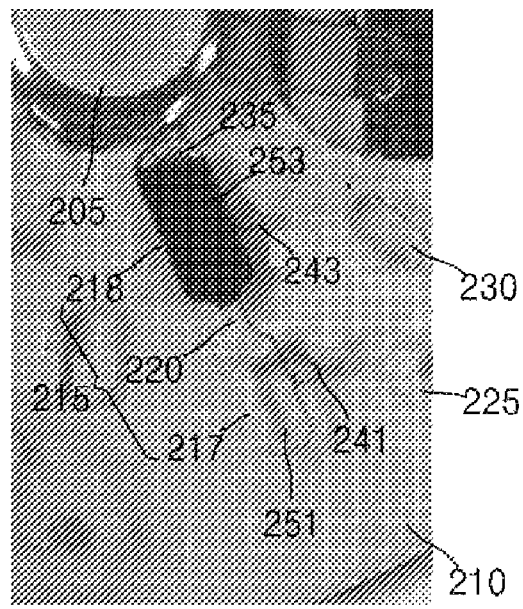
FIGS. 6A through 6H are photographs sequentially illustrating experimental results obtained by using a method of separating components using the apparatus of FIG. 5 according to another exemplary embodiment of the present invention.
Figure 6B:
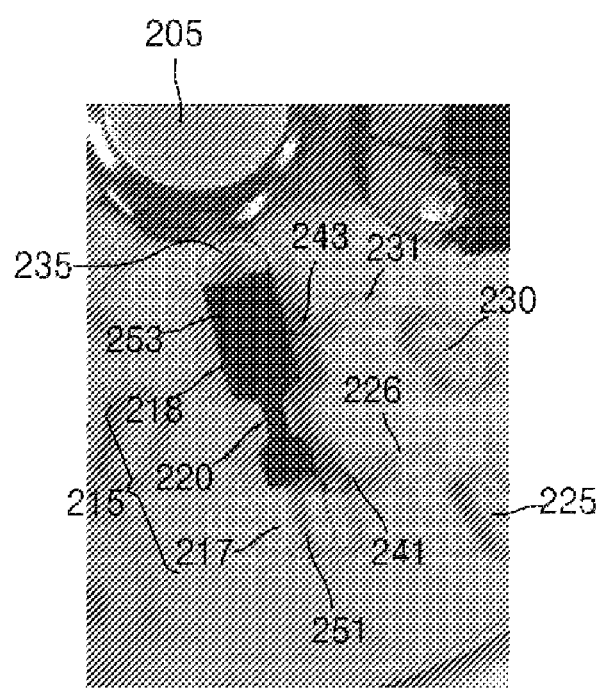
Figure 6C:
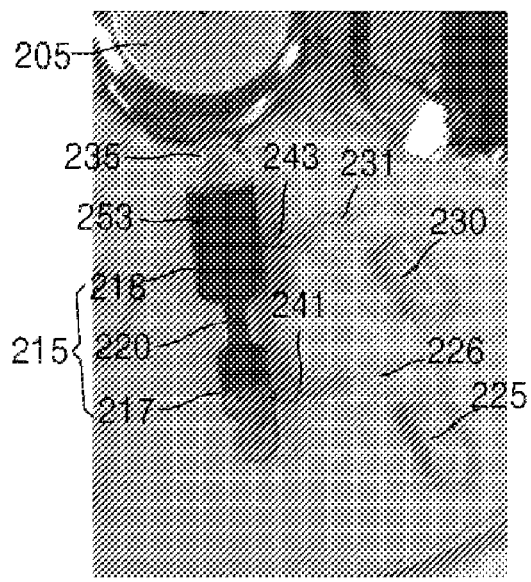
Figure 6D:
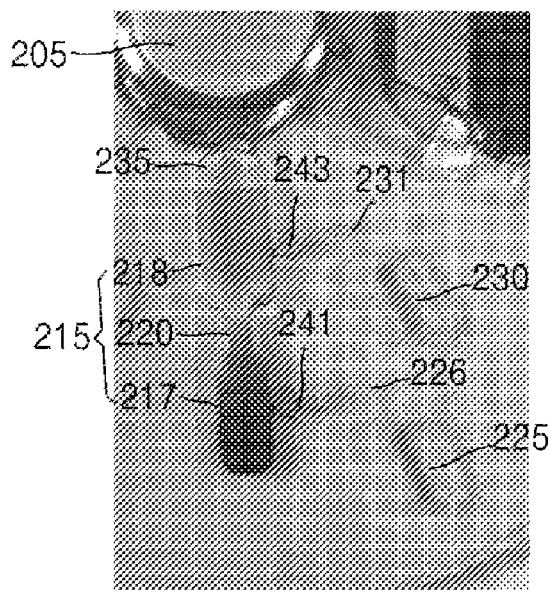
Figure 6E:
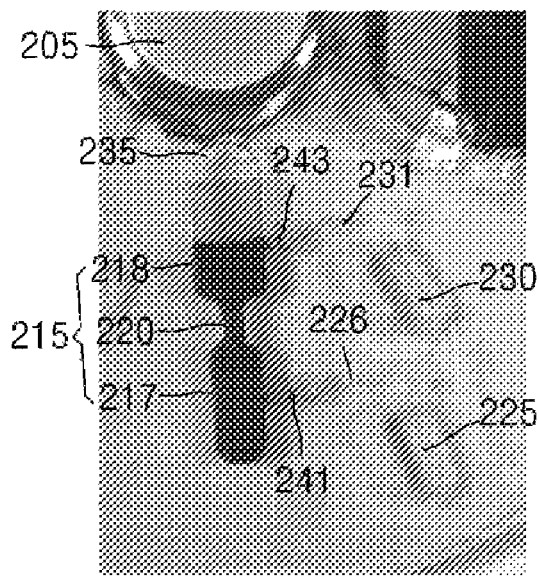

Referring to FIG. 6A, 100 μl of a DGM 251 is injected through the inlet hole 235 into the main chamber 215, and the spindle motor 205 is driven to pump the DGM 251 such that the DGM 251 is filled in the first liquid receiving part 217. A diluted blood solution 253 prepared by mixing 100 μl of WB, 100 μl of salt solution having a concentration of 0.9%, and a small amount of anticoagulant is injected through the inlet hole 235 into the main chamber 215. The diluted blood solution 253 is filled in the second liquid receiving part 218. The capillary tube 220 is filled with air that is yet to be discharged. Accordingly, the DGM 251 in the first liquid receiving part 217 and the diluted blood solution 253 in the second liquid receiving part 218 are isolated from each other.

Figure 6F:
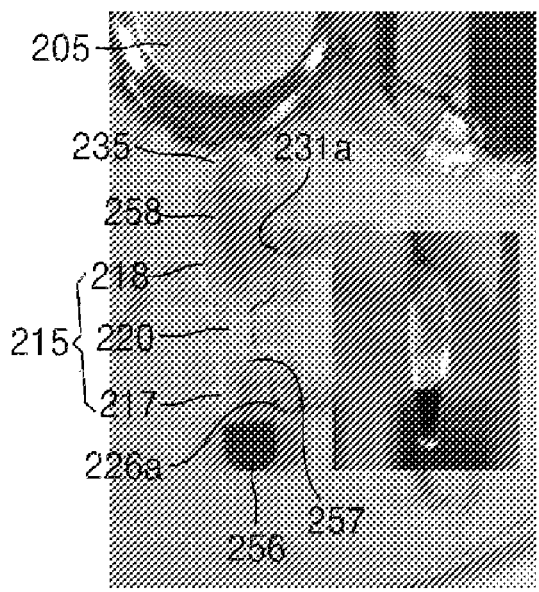

Referring to FIGS. 6B through 6E, when the spindle motor 205 is driven again to rotate the substrate 210, the diluted blood solution 253 passes through the capillary tube 220 and gradually penetrates into the DGM 215, and a plurality of layers begin to be formed. Referring to FIG. 6F, when the substrate 310 is rotated for 5 minutes or more at 3000 to 3500 rpm, first through third layers 256, 257, and 258 are formed according to density. The first layer 256 is a deep red liquid containing a great number of RBCs, and has a highest density. The second layer 257 is a colorless liquid containing a great number of WBCs which are specific components desired to be extracted, and has a density less than that of the first layer 256. The third layer 258 is a pale red liquid hardly containing RBCs and WBCs, and has a lowest density.

Figure 6G:
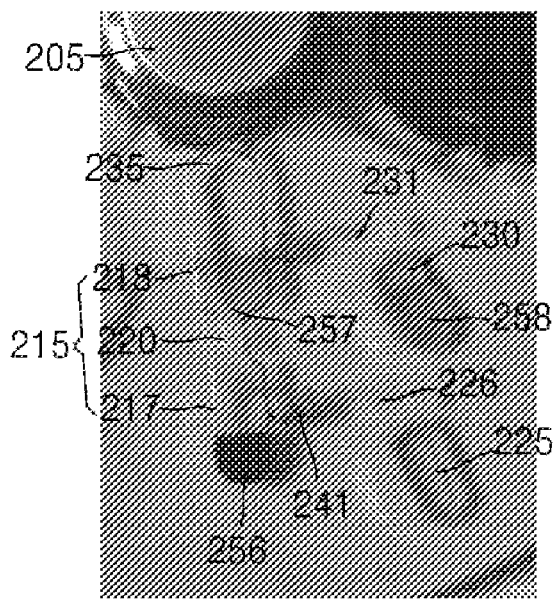
Figure 6H:
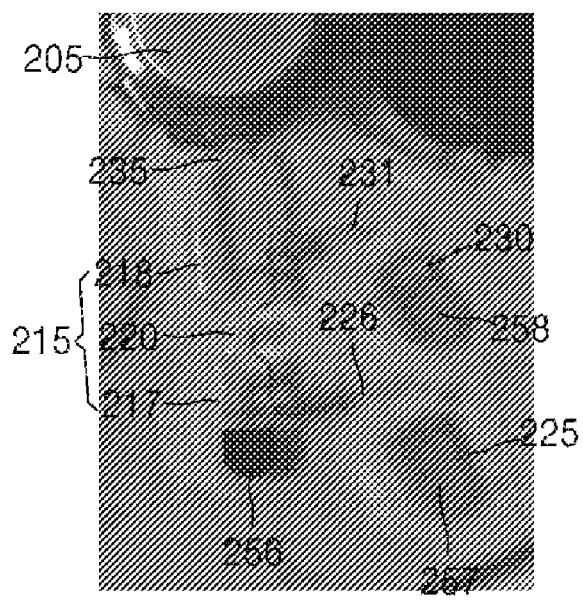

The interface between the first layer 256 and the second layer 257 is almost at the same level with the first channel connecting part 226a, and the interface between the second layer 257 and the third layer 258 is almost at the same level with the second channel connecting part 231a. Referring to FIG. 6G, when the closed second channel 231 is opened and the substrate 210 is rotated, the third layer 258 is pumped and discharged from the main chamber 215 to the waste chamber 230. Referring to FIG. 6H, when the closed first channel 226 is opened and the substrate 210 is rotated, the second layer 257 is pumped and discharged from the main chamber 215 to the component separating chamber 225.

A method of manufacturing the apparatus 200 will now be explained in detail with reference to FIGS. 1 and 5. Since the method of manufacturing the apparatus 200 to be described with reference to FIGS. 1 and 5 is similar to the method of manufacturing the apparatus 100 described with reference to FIGS. 1 and 2, the following explanation will be made focusing on the difference therebetween.

To determine the positions of the first channel connecting part 226a where the component separating chamber 225 is connected to the main chamber 215 and the second channel connecting part 231a where the waste chamber 230 is connected to the main chamber 215, data as shown in table 1 should be accumulated in advance as described above. The first channel connecting part 226a is formed at a position spaced by a distance of 67 µl, corresponding to the average volume of the first layer 31, from an end 215a of the main chamber 215, when the first channel 226 is formed on the substrate 210. The second channel connecting part 231a is formed at a position spaced by a distance 175 µl, corresponding to the sum of the average volume of the first layer 31 and the average volume of the second layer 32, from the end 215a of the main chamber 215, when the second channel 231 is formed on the substrate 210. As a result, the first channel connecting part 226a is located approximately in the middle of the first liquid receiving part 217, and the second channel connecting unit 231a is located approximately in the middle of the second liquid receiving part 218 as described above.

Hence, the liquid discharged to the waste chamber 230 after the plurality of layers are formed (see FIG. 6F) has most of the third layer 258 (see FIG. 6G), and has no or a small amount of the second layer 257. The liquid discharged to the component separating chamber 225 has most of the second layer 257 (see FIG. 6H), and has no or a small amount of the first layer 256 or the third layer 258.

Figure 7A:
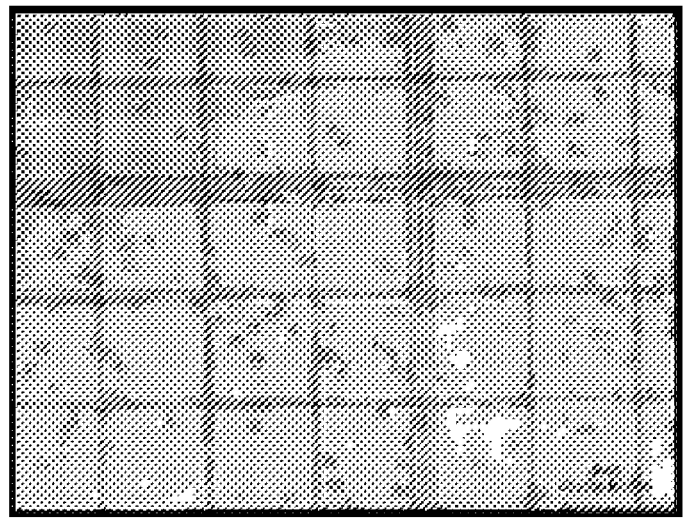
FIGS. 7A and 7B are enlarged photographs respectively illustrating a component separating chamber and a waste chamber of FIG. 6H.
Figure 7B:
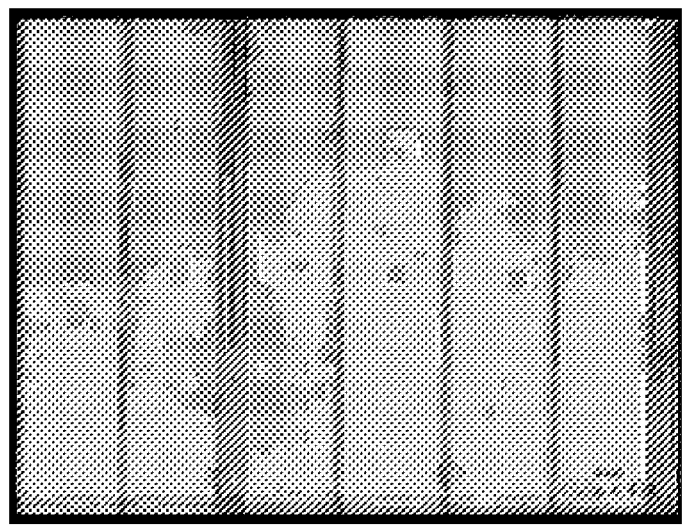

FIGS. 7A and 7B are enlarged photographs respectively illustrating the component separating chamber 225 and the waste chamber 230 of FIG. 6H. Referring to FIG. 7A, the component separating chamber 225 contains a great number of WBCs indicated by small spots. Referring to FIG. 7B, the waste chamber 230 hardly contains WBCs indicated by small spots.

Table 2 shows the numbers of WBCs contained in the second layer 32 and the third layer 33 (see FIG. 1B) measured after the related art method of separating components through centrifugation was performed four times. Table 3 shows the numbers of WBCs contained in the component separating chamber 225 and the waste chamber 230 measured after the method of separating components using the apparatus 200 according to the present invention was performed two times.

TABLE 2

|  | First experiment | Second experiment | Third experiment | Fourth experiment | Average |
|---|---|---|---|---|---|
| Number of WBCs in second layer | 54400 | 59040 | 40720 | 74240 | 57100 |
| Number of WBCs in third layer | 0 | 0 | 3547 | 0 | 887 |

TABLE 3

|  | First experiment | Second experiment | Average |
|---|---|---|---|
| Number of WBCs in component separating chamber | 27000 | 30400 | 28700 |
| Number of WBCs in waste chamber | 660 | 1200 | 909 |

Considering that data of Table 2 were obtained by those skilled in centrifugation experiments, and data of Table 3 were obtained by the inventors of the present invention unskilled in centrifugation experiments, it can be found that a sufficient number of WBCs necessary for diagnosing diseases can be reliably obtained using the apparatus 200 according to the present invention.

While the WBCs are extracted from the WB in the FIGS. 3A through 3E, the method of separating the specific components according to the present invention is not limited thereto. For example, specific components may be extracted from another sample such as sputum, urine, or saliva.

Also, while the component separating apparatus includes only one component separating chamber in FIGS. 2 and 5, the present invention may involve a component separating apparatus including a plurality of component separating chambers, and a method of separating and extracting a plurality kinds of specific components.

As described above, specific components can be separated from a sample at a constant yield regardless of an operator's skill level. Also, contamination factors during an operation of separating the specific components can be reduced, and thus the risk of failure to separate the necessary specific components and of misdiagnosis due to contaminated specific components can be reduced.

While the present invention has been particularly shown and described with reference to exemplary embodiments thereof, it will be understood by those of ordinary skill in the art that various changes in form and details may be made therein. For example, unlike in FIGS. 2 and 5, the apparatus according to the present invention may include a plurality of component separating chambers and separate a variety of specific components using the plurality of component separating chambers. Accordingly, the spirit and scope of the present invention is defined only by the following claims.

What is claimed is:

1. An apparatus for separating components, the apparatus comprising:
a main chamber which contains a sample that is separated into a plurality of layers by a centrifugal force;
a component separating chamber which is connected to the main chamber, and contains a specific layer including specific components among the plurality of layers within liquid receiving parts;
a first channel which connects the component separating chamber to the main chamber; and
a first channel valve which is disposed in the first channel to control a liquid flowing through the first channel.

2. The apparatus of claim 1, wherein the main chamber and the component separating chamber are formed on a single substrate.

3. The apparatus of claim 2, further comprising a rotating unit which rotates the substrate.

4. The apparatus of claim 3, wherein the main chamber extends in a direction parallel to a direction of a centrifugal force produced by the rotation of the substrate.

5. The apparatus of claim 3, wherein the component separating chamber is disposed to pump the specific layer from the main chamber into the component separating chamber due to a centrifugal force produced by the rotation of the substrate.

6. The apparatus of claim 1, further comprising:
a waste chamber which is connected to a portion of the main chamber to which the component separating chamber is not connected, and receives a layer not including the specific components among the plurality of layers formed in the main chamber;
a second channel which connects the waste chamber to the main chamber; and
a second channel valve which is disposed on the second channel to control a liquid flowing through the second channel.

7. The apparatus of claim 6, further comprising a rotating unit rotating the substrate, wherein the main chamber, the component separating chamber, and the waste chamber are formed on a single substrate, and the waste chamber is disposed to pump the layer not including the specific components from the main chamber into the waste chamber due to a centrifugal force produced by the rotation of the substrate.

8. The apparatus of claim 1, further comprising one or more additional component separating chambers in addition to the component separating chamber, which are used to extract and receive one or more additional specific layers among the plurality of layers formed in the main chamber, and one or more additional channels and additional channel valves in addition to the first channel and the first channel valve respectively corresponding to the one or more additional component separating chambers.

9. The apparatus of claim 8, wherein the one and more additional component separating chambers and the component separating chamber are connected to different portions of the main chamber.

10. The apparatus of claim 1, wherein the main chamber comprises at least one pair of liquid containing parts, and at least one capillary tube which connects adjacent liquid containing parts.

11. The apparatus of claim 10, wherein some of the liquid containing parts contain the sample, the remaining ones of the liquid containing parts contain a reagent that reacts with the sample and helps the sample to be separated into the plurality of layers, and the at least one capillary tube isolates the sample from the reagent before the sample is separated into the plurality of layers.

12. The apparatus of claim 6, further comprising one or more additional component separating chambers in addition to the component separating chamber, which are used to extract and receive one or more additional specific layers among the plurality of layers formed in the main chamber, one or more additional channels and additional channel valves in addition to the first channel and the first channel valve respectively corresponding to the one or more additional component separating chambers, and an energy source which supplies energy to the first channel valve, the second channel valve and the one or more additional channel valves that open corresponding channels, wherein the first channel valve, the second channel valve and the one or more additional channel valves include a phase change material that closes the corresponding channels and is in a solid state at room temperature and is in a liquid state when supplied with energy.

13. The apparatus of claim 12, wherein the first channel valve, the second channel valve and the one or more additional channel valves further comprise a plurality of micro heating particles which are dispersed in the phase change material and produce heat when supplied with the energy.

14. The apparatus of claim 12, wherein the energy source emits an electromagnetic wave to the first channel valve, the second channel valve or the one or more additional channel valves.

15. The apparatus of claim 14, wherein the energy source includes a laser source which emits a laser beam.

16. A method of separating specific components from a sample using an apparatus for separating components, the method comprising:
injecting the sample into a main chamber of the apparatus;
separating the sample into a plurality of layers according to components; and
opening a first channel valve disposed in a first channel connecting the main chamber to a component separating chamber of the apparatus and extracting and discharging a specific layer including the specific components among the plurality of layers within liquid receiving parts to the component separating chamber.

17. The method of claim 16, wherein the sample is one selected from the group consisting of whole blood (WB), sputum, urine, and saliva.

18. The method of claim 16, wherein the sample is whole blood (WB), and the extracting and discharging of the specific layer including the specific components comprises extracting and discharging a layer which includes more of the specific components than any other layers to the component separating chamber.

19. The method of claim 18, wherein the specific components discharged to the component separating chamber are cells or viruses.

20. The method of claim 19, wherein the cells are white blood cells (WBC).

21. The method of claim 16, further comprising injecting a reagent, which reacts with the sample and helps the sample to be separated into the plurality of layers, into the main chamber.

22. The method of claim 21, wherein the reagent is a density gradient medium (DGM).

23. The method of claim 21, wherein the injecting of the reagent into the main chamber precedes the injecting of the sample into the main chamber.

24. The method of claim 21, wherein
before the separating of the sample into the plurality of layers, the sample and the reagent are injected into different liquid receiving parts of the main chamber such that the sample and the reagent are isolated from each other with the at least one capillary tube therebetween.

25. The method of claim 16, wherein the separating of the sample into the plurality of layers comprises applying a centrifugal force to the sample contained in the main chamber and accelerating the separation of the sample into the plurality of layers.

26. The method of claim 16, wherein the extracting and discharging of the specific layer including the specific components comprises applying a centrifugal force to the plurality of layers and pumping the specific layer from the main chamber into the component separating chamber.

27. The method of claim 16, wherein
the method further comprises opening a second channel valve of a second channel which connects a waste chamber to a portion of the main chamber to which the component separating chamber is not connected and discharging a layer not including the specific components among the plurality of layers to the waste chamber after the separating of the sample into the plurality of layers.

28. The method of claim 27, wherein the discharging of the layer not containing the specific components to the waste chamber comprises applying a centrifugal force to the plurality of layers and pumping the layer not containing the specific components from the main chamber into the waste chamber.

29. The method of claim 28, wherein the discharging of the layer not containing the specific components to the waste chamber precedes the extracting and discharging of the specific layer including the specific components.

30. The method of claim 16, wherein the apparatus comprises one or more additional component separating chambers in addition to the component separating chamber, and one or more additional channels and additional channel valves respectively corresponding to the one or more additional component separating chambers, and the extracting and discharging of the specific layer including the specific components comprises respectively extracting and discharging additional specific layers to the one or more additional component separating chambers.

31. The method of claim 27, wherein energy is supplied to the first and second channel valves to open the first and second channels valves by melting a phase change material of the first and second channel valves that closes corresponding channels and is in a solid state at room temperature and in a liquid state when supplied with energy.

32. The method of claim 31, wherein a plurality of micro heating particles are dispersed in the phase change material and produce heat when supplied with the energy.

33. The method of claim 31, wherein the energy supplied to the valve is an electromagnetic wave.

34. The method of claim 33, wherein the electromagnetic wave is a laser beam.

* * * * *